US006199812B1

(12) United States Patent
Schuepbach (10) Patent No.: US 6,199,812 B1
(45) Date of Patent: Mar. 13, 2001

(54) SWIVEL ARM, ESPECIALLY FOR A SURGICAL MICROSCOPE STAND (75) Inventor: Rolf Schuepbach, Diepoldsau (CH)

(73) Assignee: Leica Microsystems AG, Heerbrugg (CH)

( * ) Notice: Subject to any disclaimer, the term of this patent is extended or adjusted under 35 U.S.C. 154(b) by 0 days.

(21) Appl. No.: 09/590,226

(22) Filed: Jun. 8, 2000

Related U.S. Application Data (63) Continuation of application No. 09/214,981, filed as application No. PCT/EP98/02909 on May 18, 1998.

(30) Foreign Application Priority Data

May 20, 1997 (CH) .................................................. 1162/97

(51) Int. Cl.⁷ .................................................. F16M 11/12
(52) U.S. Cl. ................ 248/324; 248/123.11; 248/292.11
(58) Field of Search ............................ 248/431, 123.11, 248/163.2, 278.1, 279.1, 280.11, 281.11, 324, 292.11; 359/368, 381, 384

(56) References Cited

U.S. PATENT DOCUMENTS

| 3,269,684 | 8/1966 | Iggulden ...................... 248/280.11 |
| 4,277,044 | 7/1981 | Hamilton ........................... 248/571 |
| 4,500,251 | 2/1985 | Kiryn et al. ........................ 414/719 |
| 5,014,693 | 5/1991 | Wright, II et al. ............. 128/204.18 |
| 5,037,267 | 8/1991 | Warner et al. ...................... 414/744 |
| 5,377,371 | 1/1995 | Foster .................................. 5/503.1 |

FOREIGN PATENT DOCUMENTS

| 0 293 228 A2 | 11/1988 | (EP) . |
| 0 628 290 A1 | 12/1994 | (EP) . |
| WO 98/52484 | 11/1998 | (WO) . |

Primary Examiner—Ramon O. Ramirez
Assistant Examiner—Jon Szumny
(74) Attorney, Agent, or Firm—Simpson, Simpson & Snyder, L.L.P.

(57) ABSTRACT

A swivel arm assembly for connecting a surgical microscope to a stand comprises a microscope interface connected to a suspension device by a swivel arm. The swivel arm includes an approximately isosceles two-armed support lever and an approximately isosceles two-armed operating lever pivotal relative to the support lever about an axle connecting the vertices of each lever. An upper shaft at an upper end of the support lever and a lower shaft at a lower end of the support lever are coupled connected to respective upper and lower operating ends of the operating lever by toggle joints, whereby moments arising at one shaft are transmitted to the other shaft at a 1:1 ratio. The swivel arm is guided for motion in a vertical plane by a parallel carriage guide having a first and second orthogonal carriage guides, and an adjustable carriage guide connects the upper shaft to the suspension device to permit the center of gravity of loading to be moved. The invention keeps the surgical microscope stable and free of play without using parallelogram supports.

15 Claims, 8 Drawing Sheets

SWIVEL ARM, ESPECIALLY FOR A SURGICAL MICROSCOPE STAND

CROSS-REFERENCES TO RELATED APPLICATIONS

The present application is a continuation of U.S. patent application Ser. No. 09/214,981 filed Feb. 16, 1999, which was the National Stage of International Application No. PCT/EP98/02909 filed May 18, 1998.

STATEMENT REGARDING FEDERALLY SPONSORED RESEARCH OR DEVELOPMENT

Not Applicable.

REFERENCE TO A"MICROFICHE APPENDIX"

Not Applicable.

BACKGROUND OF THE INVENTION

1. Field of the Invention

The present invention relates to generally to support arms forming part of an articulated stand for supporting a load, and particularly to a swivel arm for transmitting torque between a pair of rotating shafts in a stand, for example a surgical microscope stand.

2. Description of the Related Art

More and more surgical microscopes are used in surgery. Because of their high intrinsic weight, they must be supported by stands. Several well-known manufacturers have put stands on the market, and from a mechanical and static perspective they correspond well to the load-carrying requirements of the surgical microscope. For example, the assignee of the present application markets stands with the designation OH, which were manufactured by Mitaka. An example of such a stand can be found in European Patent Publication No. 628290. A further development of this stand is described in commonly owned PCT International Publication No. WO 97/13997.

Most of the more recent stands utilize parallelogram support arms to bear the weight of the surgical microscopes over the greatest possible distances without bending or distortion, so that the freedom of movement and the operating radius of the microscopes are as large as possible. For example, the aforementioned EP-A-628290 presents such a construction. The stand of EP-A-628290 also provides a parallelogram "swivel arm" for the swiveling support of a surgical microscope directly attached thereto. The purpose of the parallelogram support arms is to conduct retention forces for the load, i.e. for the surgical microscope, to the stand so that the microscope remains stable in its position when brakes on the stand are locked. There is a need for two adjustable carriage guides for the two upper parallel supports of a conventional parallel guide bar arrangement.

BRIEF SUMMARY OF THE INVENTION

An object of the present invention is the further development of this known "swivel arm." In particular, parallelogram support arms will be abandoned, but a distortion-free bearing arrangement of a surgical microscope will still be possible. The operating radius may not be restricted, and the construction should be stable, user-friendly, and as free from play as possible.

This object is realized by replacing the parallelogram supports with a combination of two approximately isosceles 2-segment angle levers, one being a support lever and the other being an operating lever. The two angle levers are connected to each other in a rotating manner and also have on both ends an identical linkage to transmit moments between an upper shaft and a lower shaft so that the center of gravity of the load can be kept in space, comparable to a parallelogram support.

In accordance with a further development of the invention, the new type of angle support is equipped with a parallel carriage guide, which maintains the angular orientation of the angle levers in space.

In contrast to the prior art, the new construction also obviates the need for two adjustable carriage guides for the two upper parallel supports of a conventional parallel guide bar arrangement. A single adjustable carriage guide is sufficient for the horizontal displacement of the load application point.

A construction with automatic balancing corresponding to the teaching of PCT International Publication No. WO 97/13997 obviously lies within the scope of the present invention. In this context the publication is considered to be disclosed, being incorporated reference.

The invention can preferably be used with a stand in accordance with Publication No. WO 97/13997, however it is not limited to such use.

BRIEF DESCRIPTION OF THE SEVERAL VIEWS OF THE DRAWINGS

The nature and mode of operation of the present invention will now be more fully described in the following detailed description of the preferred embodiments taken with the accompanying drawing figures, in which.

DETAILED DESCRIPTION OF THE PREFERRED EMBODIMENTS

Figure 1:
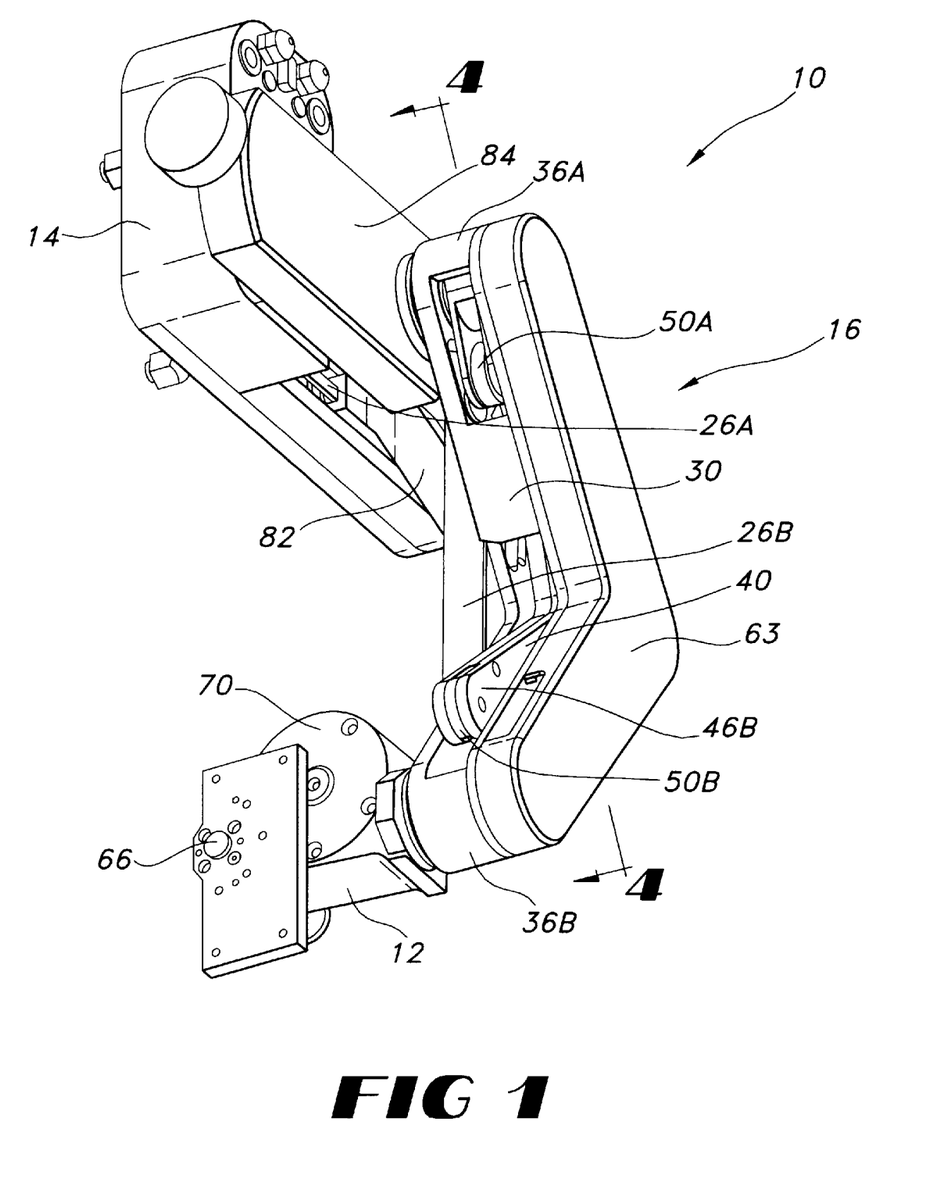
FIG. 1 is a perspective view showing a swivel arm assembly formed in accordance with a preferred embodiment of the present invention.
Figure 2:
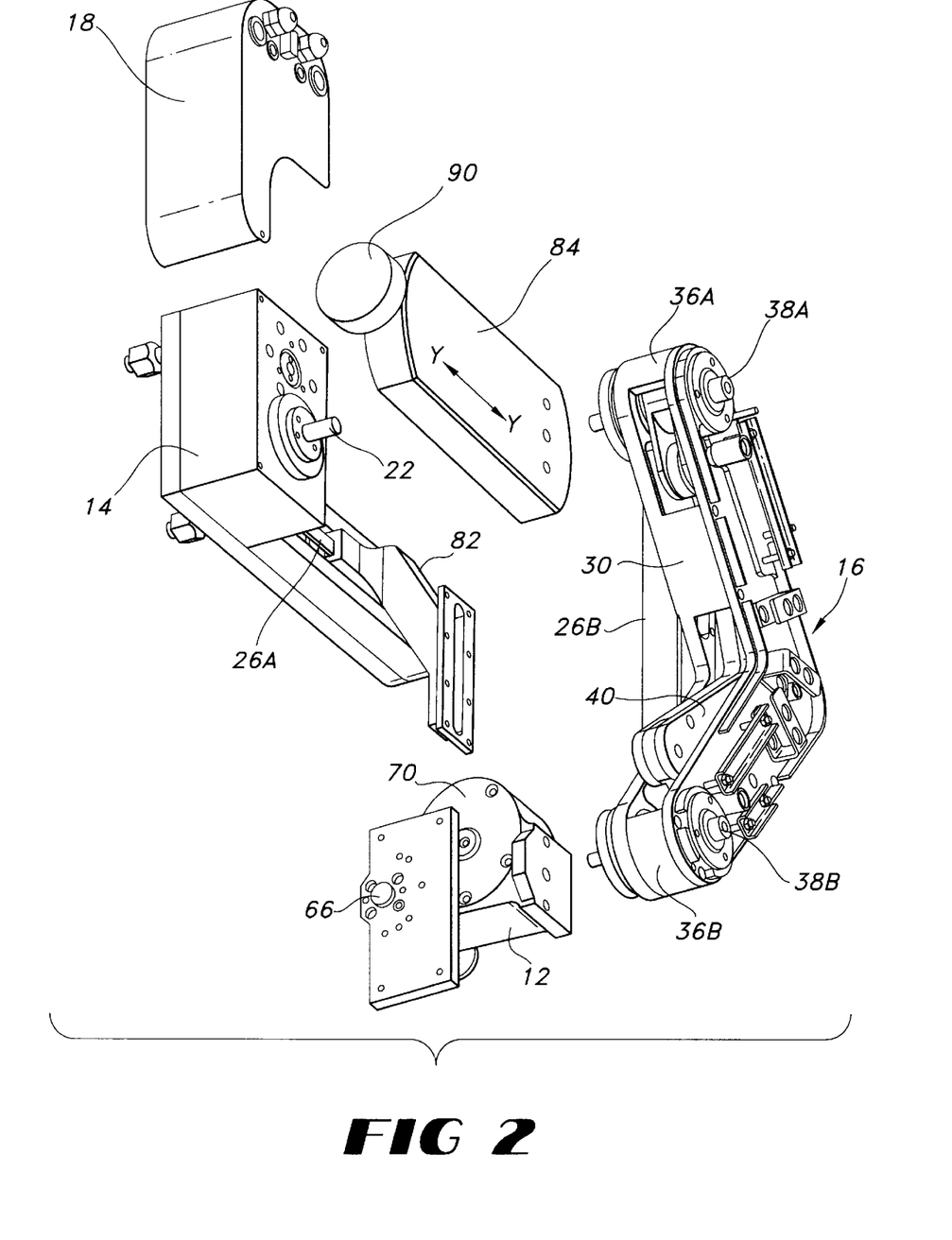
FIG. 2 is an exploded view of the swivel arm assembly shown in FIG. 1.

Referring initially to FIGS. 1 and 2, a swivel arm assembly formed in accordance with a preferred embodiment of the present invention is shown and designated by the reference numeral 10. Swivel arm assembly 10 generally comprises a microscope interface 12 connected to a suspension device 14 by way of a swivel arm 16. Swivel arm assembly 10 is used to suspend a microscope (not shown), most commonly a surgical microscope, from a microscope support stand (also not shown). The construction of the stand is secondary and does not form part of the present invention, although a stand in accordance with PCT International Publication No. WO 97/13997 is preferred.

Figure 8:
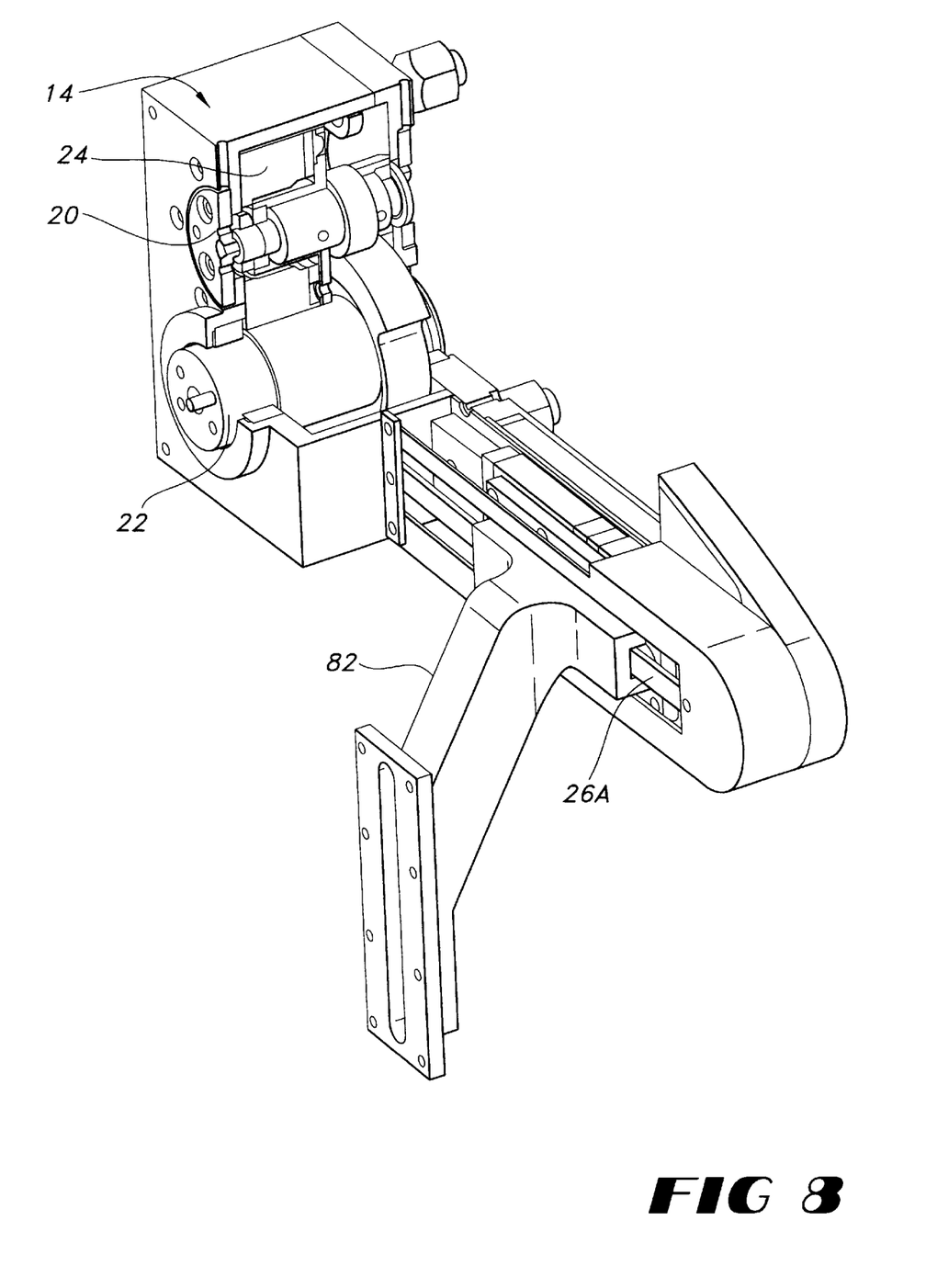
FIG. 8 is a partially sectioned perspective view of a suspension device for mounting the swivel arm assembly of the present invention on a surgical microscope stand.

Suspension device 14, shown also in FIG. 8, includes an adapter 18 and a stand interface 20 via which the suspension device is connected or can be connected to a stand. Suspension device 14 further includes a rotatable axle 22 and a brake 24 operable to selectively prevent rotation of axle 22. Finally, suspension device includes a first carriage guide 26A forming a part of the connection between swivel arm 16 and suspension device 14.

Referring also now to FIGS. 4 through 7, swivel arm 16 includes a support lever 30 having a center portion 32 and a pair of approximately isosceles arm portions 34A, 34B extending from center portion 32 to provide a remote upper end 36A and a remote lower end 36B. An upper shaft 38A is supported at upper end 36A in a manner that permits rotation of the upper shaft about its axis relative to support lever 30. Likewise, a lower shaft 38B having an axis parallel to that of upper shaft 38A is supported at lower end 36B in a manner that permits rotation of the lower shaft about its axis relative to support lever 30.

Swivel arm 16 also includes an operating lever 40 having a center portion 42 and a pair of approximately isosceles arm portions 44A, 44B extending from center portion 42 to provide a remote upper operating end 46A and a remote lower operating end 46B. Operating lever 40 rotates relative to support lever 30 on bearings mounted on a bearing axle 48 aligned through center portions 32 and 42 of the support lever and operating lever, respectively.

The upper and lower operating ends 46A, 46B of operating lever 40 are linked to upper and lower shafts 38A, 38B by toggle joints 50A, 50B, respectively. Toggle joints 50A, 50B each include a pair of toggle links 52 and 54. In upper toggle joint 50A, toggle link 52 has one end pivotally coupled to upper operating end 46A by a pivot 56 and an opposite end pivotally coupled to an end of toggle link 54 by a pivot 58. An end of toggle link 54 opposite from pivot 58 is coupled to upper shaft 38A in a torsionally rigid manner. Lower toggle joint 50B is arranged similarly to upper toggle joint 50A, such that toggle link 52 has one end pivotally coupled to lower operating end 46B by a pivot 60 and an opposite end pivotally coupled to an end of toggle link 54 by a pivot 62. An end of toggle link 54 opposite from pivot 62 is coupled to lower shaft 38B in a torsionally rigid manner. Consequently, moments arising about lower shaft 38BB are transmitted to upper shaft 38A at a 1:1 ratio, and vice versa. At least one covering 63, preferably of foam, covers movable parts of swivel arm 16.

Figures 5, 6:
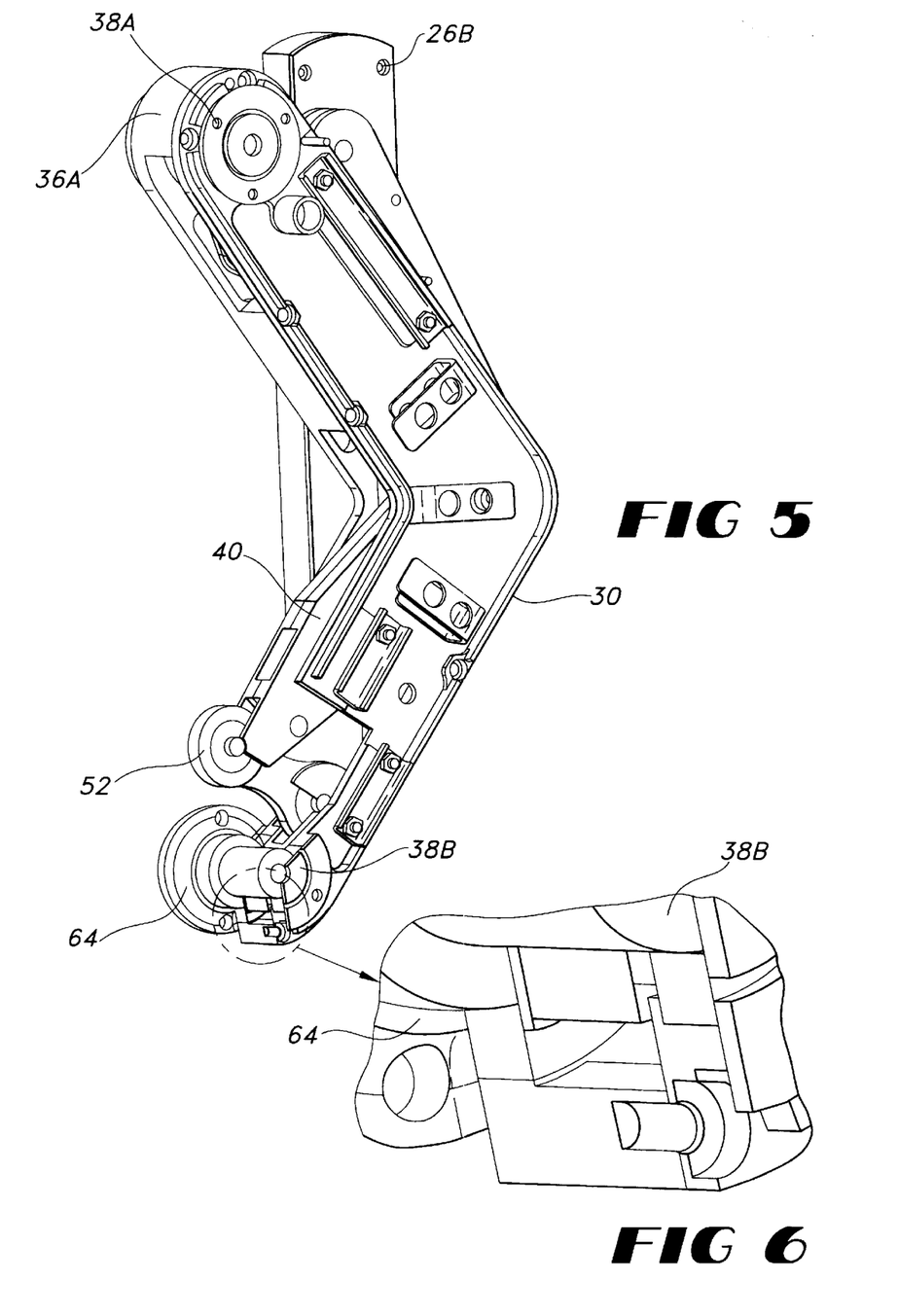
FIG. 5 is a perspective view of the swivel arm assembly of the preferred embodiment with a cover of the swivel arm assembly being removed to show further assembly details.
FIG. 6 is an enlarged view of circled area A in FIG. 5.
Figure 7:
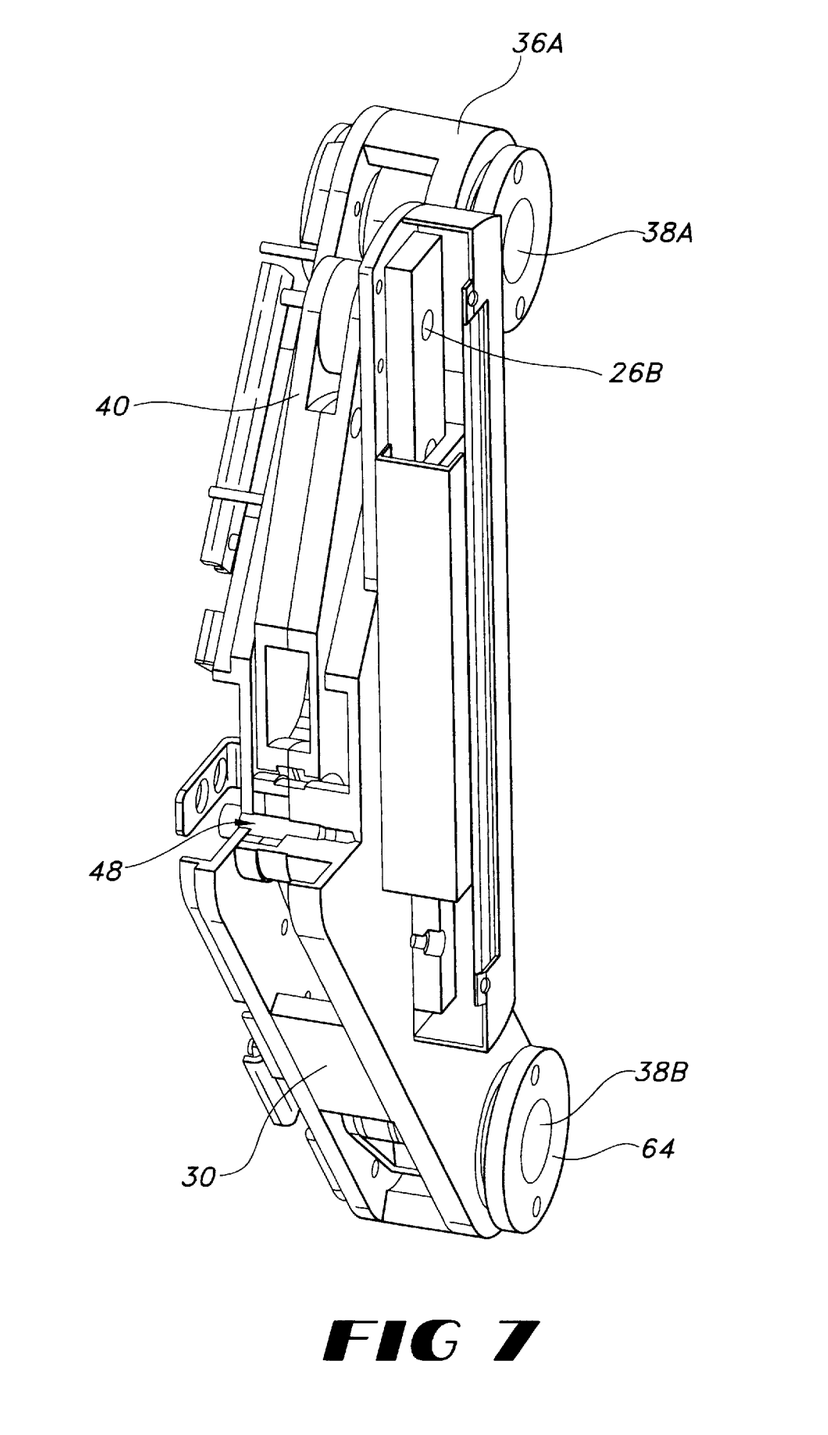
FIG. 7 is another perspective of the view of the swivel arm assembly shown in FIG. 5.
Figure 9:
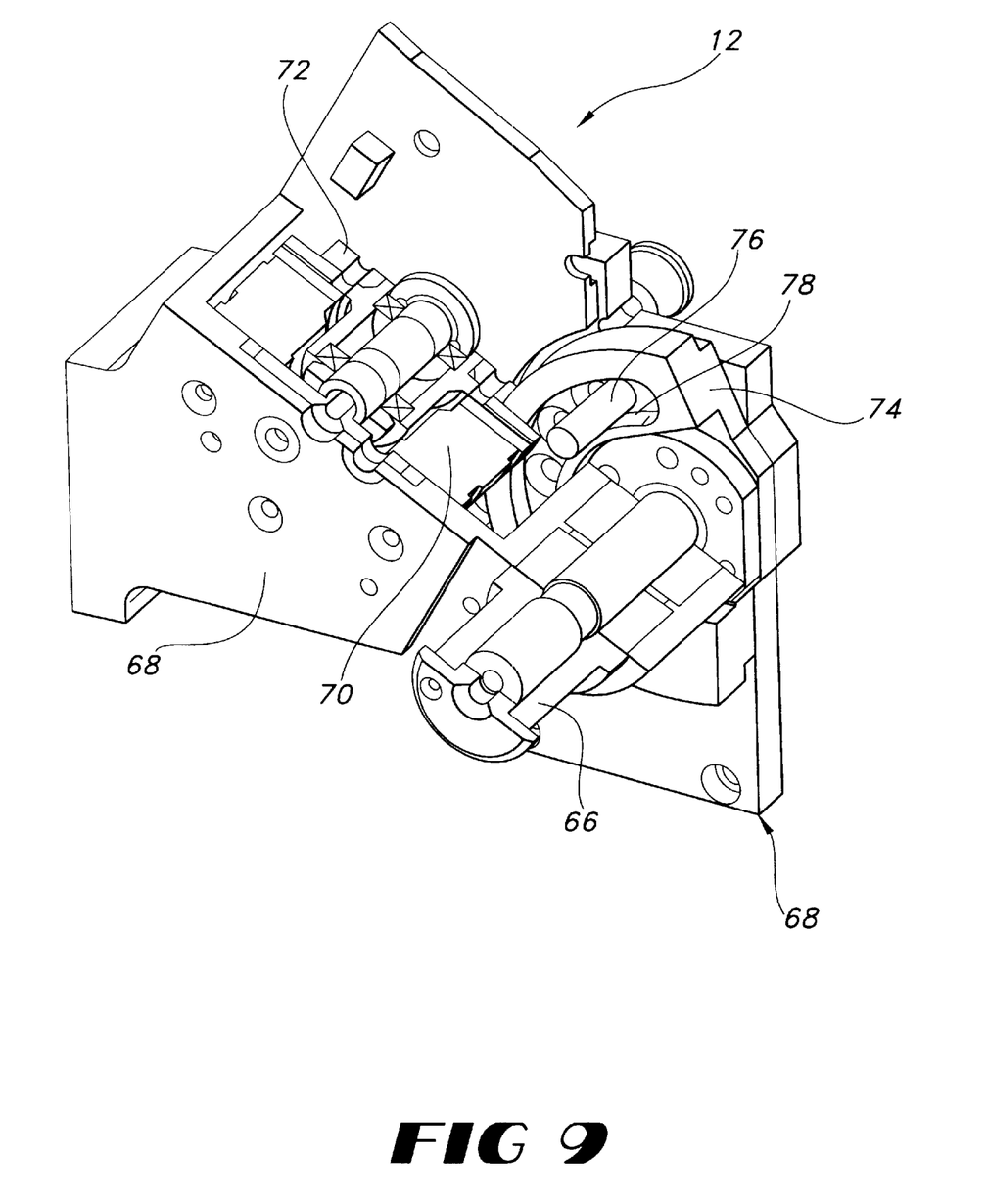
FIG. 9 shows a microscope interface for mounting a surgical microscope to the swivel arm assembly of the present invention.

FIG. 9 shows microscope interface 12 used to mount a surgical microscope on swivel arm assembly 10. A connector 64, shown in FIG. 6, is provided on lower shaft 38B to receive microscope interface 12 such that microscope interface 12 rotates together with lower shaft 38B. Microscope interface 12 supports a tilting axle 66 that has a microscope receiver 68 for mounting a surgical microscope (not shown) on the microscope interface. As can be understood, the a surgical microscope may be tilted about an axis of titling axle 66, and can also be rotated along with microscope interface 12 about an axis of lower shaft 38B. Tilting motion of tilting axle 66 is selectively prevented by applying a brake 70 that engages, via a gearwheel 72, a gearwheel segment 74 rigidly mounted on tilting axle 66. Motion of gearwheel segment 74 is limited by a peg 76 received within an arcuate slot 78 in the gearwheel segment. Tilting motion of the surgical microscope connected by way of microscope receiver 68 is thereby limited.

A preferred arrangement for connecting support lever 30 of swivel arm 16 to suspension device 14 will now be described in conjunction with FIGS. 1–5 and 7. A parallel carriage guide 80 is provided for allowing motion of the entire swivel arm 16 in a vertical plane while maintaining the angular orientation of support lever 30 and operating lever 40 in space. Parallel carriage guide 80 includes first carriage guide 26A on suspension device 14, and a second carriage guide 26B fixed to support lever 30. The two carriage guides 26A and 26B have travel axes that are orthogonal to each other, and a travel bracket 82 is slidably mounted at one end for guided travel along first carriage guide 26A and at another end for guided travel along second carriage guide 26B. Accordingly, motion of swivel arm 16 in a vertical plane, including circular arc motion, is possible.

Figure 3:
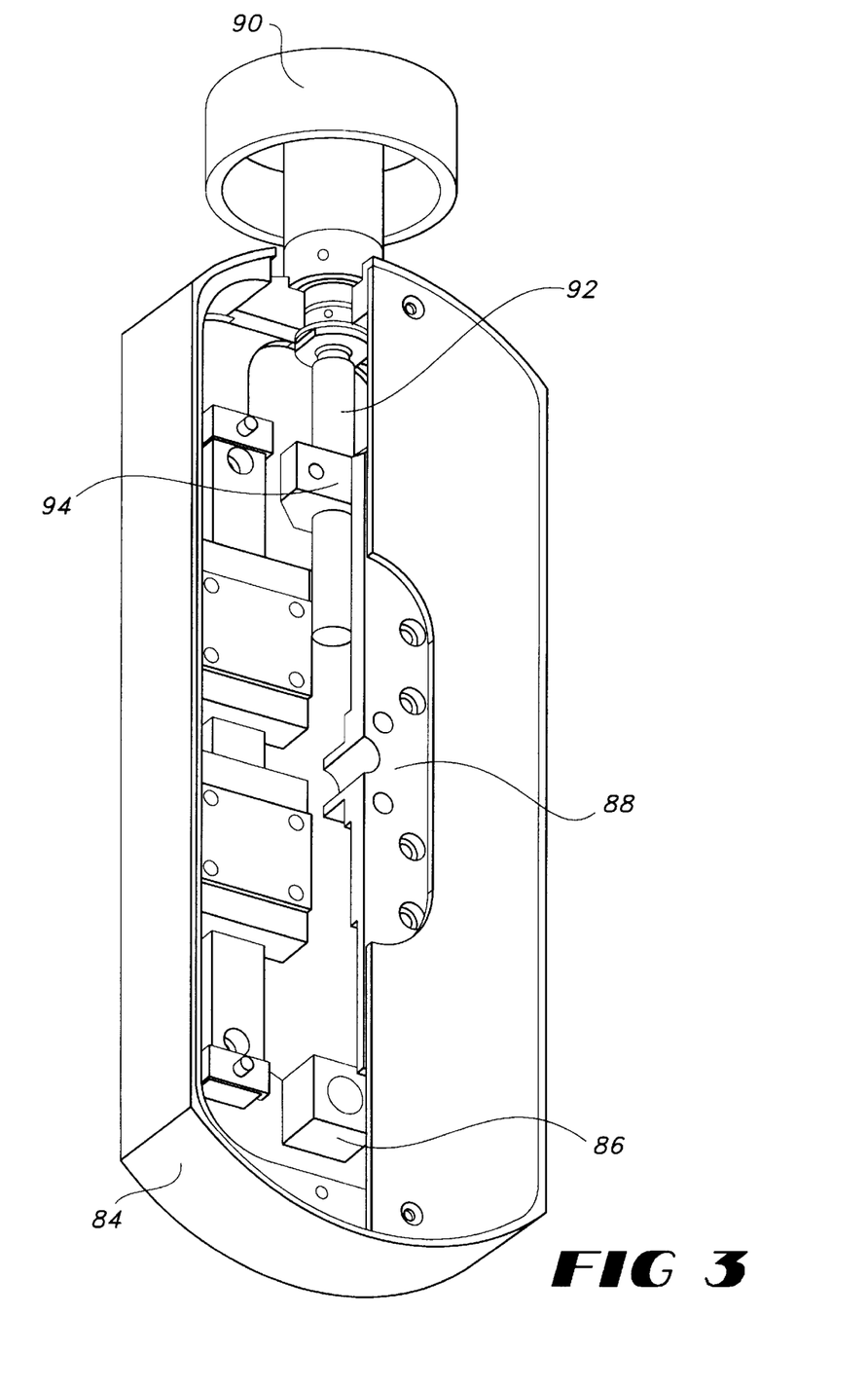
FIG. 3 is a perspective view showing an adjustable carriage guide of the swivel arm assembly shown in FIG. 1.
Figure 4:
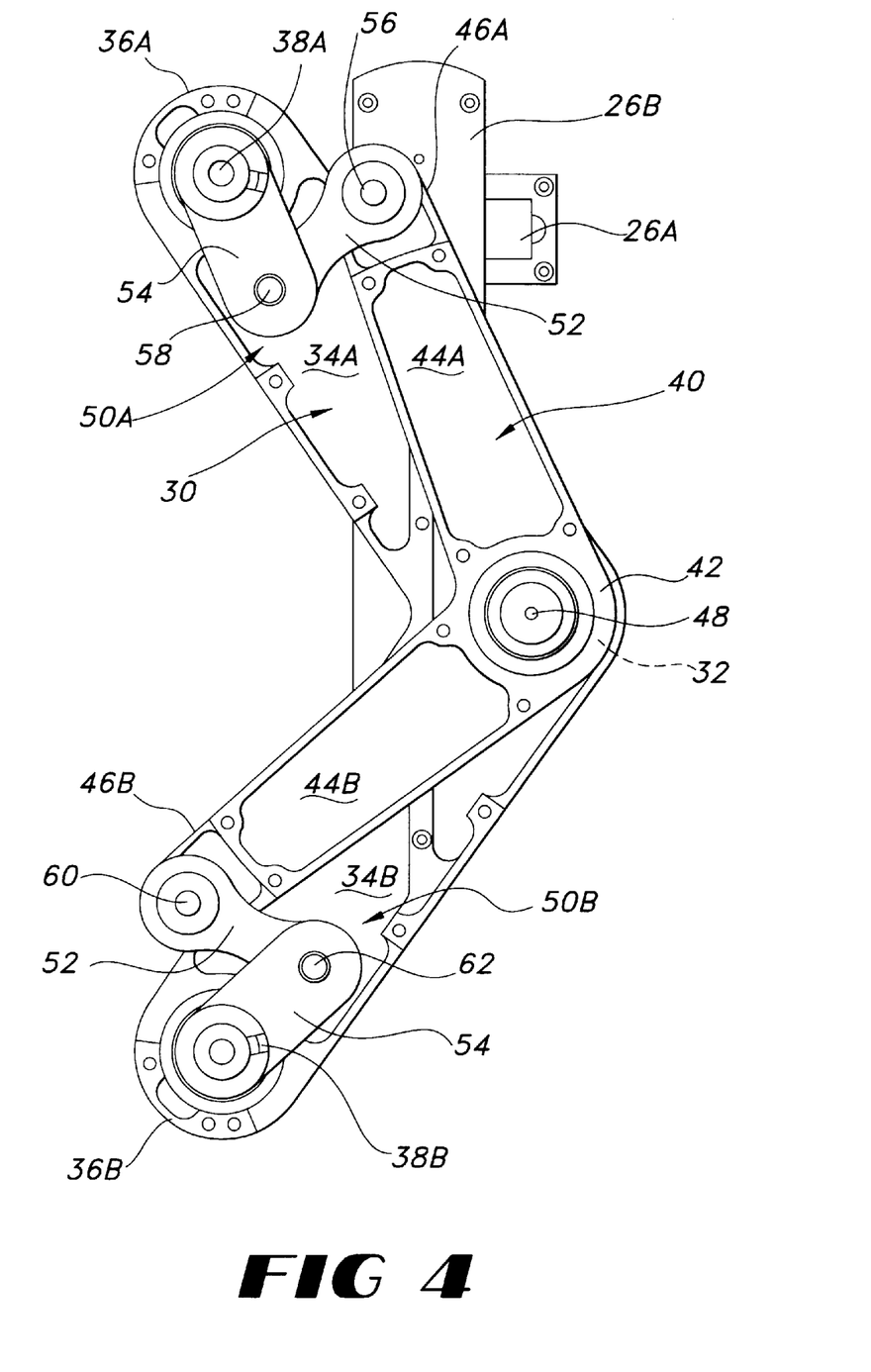
FIG. 4 is a sectional view of the swivel arm assembly of the preferred embodiment taken generally along the line 4—4 in FIG. 1.

Swivel arm assembly 10 further comprises an adjustable carriage guide 84, best seen in FIG. 3, forming an adjustable connection between upper shaft 38A and suspension device 14. Carriage guide 84 includes a first receiver 86 for receiving upper shaft 38A that passes through support lever 30 and operating lever 40, and a second receiver 88 for receiving rotatable axle 22 of suspension device 14. An adjusting knob 90 enables rotation of an adjusting spindle 92, and a screw follower 94 fixed to second receiver 88 responds by moving second receiver 88 along a direction or travel axis of the adjusting spindle. Adjustable carriage guide 84 is useful for moving the center of gravity of the load supported by upper shaft 38A to beneath a point of suspension on the stand for balancing purposes. As mentioned, this adjustment function can be automated by applying known technology.

What is claimed is:

1. A swivel arm assembly for connecting a microscope to a support stand, said swivel arm assembly comprising:

a support lever having a center portion and a pair of approximately isosceles arm portions extending from said center portion of said support lever to provide upper and lower ends spaced from said center portion of said support lever;

an upper shaft supported at said upper end for rotation relative to said support lever;

a lower shaft supported at said lower end for rotation relative to said support lever;

an operating lever having a center portion and a pair of approximately isosceles arm portions extending from said center portion of said operating lever to provide upper and lower operating ends spaced from said center portion of said operating lever;

an axle connecting said center portions of said support lever and said operating lever, said operating lever being mounted for rotation about an axis of said axle relative to said support lever;

means connecting said upper operating end of said operating lever to said upper shaft and said lower operating end of said operating lever to said lower shaft to transmit a moment arising at one of said upper and lower shafts to the other of said upper and lower shafts;

whereby rotation of said one of said upper and lower shafts causes rotation of said other of said upper and lower shafts.

2. The swivel arm assembly according to claim 1, wherein transmission of said moment is at a 1:1 ratio.

3. The swivel arm assembly according to claim 1, wherein said means connecting said upper operating end to said upper shaft includes an upper toggle joint connected to said upper operating end and said upper shaft in a torsionally rigid manner, and said means connecting said lower operating end to said lower shaft includes a second toggle joint connected to said lower operating end and said lower shaft in a torsionally rigid manner.

4. The swivel arm assembly according to claim 1, further including a suspension device mountable on said stand and a parallel carriage guide for connecting said support lever to said suspension device.

5. The swivel arm assembly according to claim 4, wherein said parallel carriage guide includes two orthogonal carriages for guiding said support lever to permit a circular arc movement of said support lever in a vertical plane.

6. The swivel arm assembly according to claim 4, further comprising a microscope interface supported by said second shaft for rotation therewith, said microscope interface including a tilting axle.

7. The swivel arm assembly according to claim 6, further comprising an adjustable carriage guide connected to said suspension device, said upper shaft being received by said adjustable carriage guide for positioning said upper shaft relative to said suspension device along a travel axis of said adjustable carriage guide.

8. The swivel arm assembly according to claim 7, wherein said adjustable carriage guide includes an adjusting knob connected to an adjusting spindle for manually adjusting the position of said upper shaft relative to said suspension device.

9. The swivel arm assembly according to claim 7, wherein said adjustable carriage guide includes an automatic position adjustment means for shifting a center of gravity of load supported by said upper shaft to beneath a point of suspension on said stand.

10. The swivel arm assembly according to claim 1, further comprising a microscope interface supported by said second shaft for rotation therewith, said microscope interface including a tilting axle.

11. The swivel arm assembly according to claim 10, wherein said microscope interface includes a brake for braking rotation of said tilting axle.

12. The swivel arm assembly according to claim 11, wherein said microscope interface includes a gearwheel segment mounted on said tilting axle for rotation therewith, said gearwheel segment having an arcuate slot formed therein, and said microscope interface includes a stop peg received within said slot for limiting rotation of said tilting axle by abutment with opposite ends of said slot.

13. The swivel arm assembly according to claim 12, wherein said brake includes a gearwheel for selectively engaging said gearwheel segment.

14. A swivel support according to claim 1, wherein said support lever includes a cover is for partially enclosing said upper and lower toggle joints and said operating lever.

15. A swivel support according to claim 14, wherein said cover includes a foam coating.

* * * * *